United States Patent
Benchemoul

(10) Patent No.: US 12,201,469 B2
(45) Date of Patent: Jan. 21, 2025

(54) CARDIOVASCULAR ACTIVITY ASSESSMENT METHOD AND DEVICE

(71) Applicant: VERMON SA, Tours (FR)

(72) Inventor: Maxime Benchemoul, Tours (FR)

(73) Assignee: VERMON SA, Tours (FR)

( * ) Notice: Subject to any disclaimer, the term of this patent is extended or adjusted under 35 U.S.C. 154(b) by 300 days.

(21) Appl. No.: 18/066,485

(22) Filed: Dec. 15, 2022

(65) Prior Publication Data
US 2023/0190223 A1  Jun. 22, 2023

(30) Foreign Application Priority Data
Dec. 20, 2021  (FR) .................................... 2113944

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/4427* (2013.01); *A61B 8/4477* (2013.01); *A61B 8/4494* (2013.01); *A61B 8/488* (2013.01); *A61B 8/54* (2013.01)

(58) Field of Classification Search
CPC ....... A61B 5/681; A61B 5/02438; A61B 8/06; A61B 8/4427; A61B 8/4494; A61B 8/488; A61B 8/54
See application file for complete search history.

(56) References Cited

U.S. PATENT DOCUMENTS

| | | |
|---|---|---|
| 5,891,039 A | 4/1999 | Bonnefous et al. |
| 2004/0138568 A1 | 7/2004 | Lo et al. |
| 2017/0231598 A1* | 8/2017 | Baek ........................ A61B 8/54 600/454 |
| 2019/0069842 A1 | 3/2019 | Rothberg et al. |

FOREIGN PATENT DOCUMENTS

FR  2759892 A1  8/1998

OTHER PUBLICATIONS

Republique Francaise Institut National De La Propriete Industrielle, Preliminary Search Report Issued in corresponding Application No. FR 2113944, dated Jul. 20, 2022.

* cited by examiner

*Primary Examiner* — Gerald Johnson
(74) *Attorney, Agent, or Firm* — Stites & Harbison, PLLC; Jeffrey A. Haeberlin

(57) ABSTRACT

A portable electronic device for assessing a human cardiovascular activity includes first and second probes substantially parallel to each other and located on either side of a third probe, substantially perpendicular to the first and second probes, each probe comprising an array of ultrasound transducers, and a control circuit configured to: a) estimate, by means of a first ultrasound beam emitted by the first probe, a position of a blood vessel with respect to the device; and b) adjust a second ultrasound beam, emitted by the third probe, according to the estimated position of the blood vessel.

15 Claims, 2 Drawing Sheets

CARDIOVASCULAR ACTIVITY ASSESSMENT METHOD AND DEVICE

TECHNICAL BACKGROUND

The present disclosure generally concerns electronic devices, and more particularly aims at devices and methods of cardiovascular activity assessment by means of ultrasounds.

PRIOR ART

Electronic devices and methods of cardiovascular activity assessment enabling, for example, to detect malfunctions likely to affect a human being's cardiovascular system, to monitor a clinical condition of a patient suffering from a cardiovascular disease, or to follow an evolution of an athlete's cardiovascular parameters during a athletic performance, are known.

SUMMARY OF THE INVENTION

An object of an embodiment is to overcome all or part of the disadvantages of known cardiovascular activity assessment methods and devices. More particularly, an object of an embodiment is to provide portable electronic device of cardiovascular activity assessment, for example, having outer dimensions compatible with its being worn on a user's wrist.

For this purpose, an embodiment provides a portable electronic device for assessing a human cardiovascular activity, comprising first and second probes substantially parallel to each other and located on either side of a third probe, substantially perpendicular to the first and second probes, each probe comprising an array of ultrasound transducers, and a control circuit configured to:
  a) estimate, by means of a first ultrasound beam emitted by the first probe, a position of a blood vessel with respect to the device; and
  b) adjust a second ultrasound beam, emitted by the third probe, according to the estimated position of the blood vessel.

According to an embodiment, a direction of emission of the second ultrasound beam is adjusted according to the estimated position of the blood vessel.

According to an embodiment, a focal distance of the second ultrasound beam is further adjusted according to the estimated position of the blood vessel.

According to an embodiment, the first ultrasound beam emitted by the first probe is adjusted according to the estimated position of the blood vessel.

According to an embodiment, the second probe is configured to emit a third ultrasound beam.

According to an embodiment, during step a), the position of the blood vessel with respect to the device is further estimated by the third ultrasound beam emitted by the second probe.

According to an embodiment, a pulse wave velocity inside of the blood vessel is estimated based on the first and third ultrasound beams respectively emitted by the first and second probes.

According to an embodiment, the blood flow rate inside of the blood vessel is further estimated, based on the second ultrasound beam, by Doppler effect.

According to an embodiment, the blood vessel is the ulnar artery.

According to an embodiment, the control circuit comprises a first pulser connected to the ultrasound transducers of the arrays of the first and second probes and a second pulser connected to the ultrasound transducers of the array of the third probe.

According to an embodiment, the control circuit comprises a single pulser coupled, via a multiplexer, to the ultrasound transducers of the arrays of the first, second, and third probes.

According to an embodiment, the array of ultrasound transducers of the third probe comprises twice more ultrasound transducers than each of the arrays of ultrasound transducers of the first and second probes, the multiplexer being a 1-to-2 multiplexer.

An embodiment provides a connected watch or bracelet comprising a device such as described.

An embodiment provides a method of assessment of a human cardiovascular activity, by a portable electronic device comprising first and second probes substantially parallel to each other and located on either side of a third probe, substantially perpendicular to the first and second probes, each probe comprising an array of ultrasound transducers, and a control circuit, the method comprising the steps of:
  a) estimating, by means of a first ultrasound beam emitted by the first probe, a position of a blood vessel with respect to the device; and
  b) adjusting a second ultrasound beam, emitted by the third probe, according to the estimated position of the blood vessel.

According to an embodiment, at step a), the position of the blood vessel with respect to the device is further estimated by a third ultrasound beam emitted by the second probe.

BRIEF DESCRIPTION OF THE DRAWINGS

The foregoing features and advantages, as well as others, will be described in detail in the rest of the disclosure of specific embodiments given by way of illustration and not limitation with reference to the accompanying drawings, in which.

DESCRIPTION OF THE EMBODIMENTS

Like features have been designated by like references in the various figures. In particular, the structural and/or functional features that are common among the various embodiments may have the same references and may dispose identical structural, dimensional and material properties.

For the sake of clarity, only the steps and elements that are useful for an understanding of the embodiments described herein have been illustrated and described in detail. In particular, the various applications of the described devices and methods have not been detailed, the described embodiments being compatible with all or most applications likely to take advantage of a device or of a cardiovascular activity estimation method. Further, the ultrasound transducers of the probes of the device have not been detailed, the forming and the practical implementation of these transducers being within the abilities of those skilled in the art based on the indications of the present disclosure.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following description, when reference is made to terms qualifying absolute positions, such as terms "front", "back", "top", "bottom", "left", "right", etc., or relative positions, such as terms "above", "under", "upper", "lower", etc., or to terms qualifying directions, such as terms "horizontal", "vertical", etc., unless otherwise specified, it is referred to the orientation of the drawings.

Unless specified otherwise, the expressions "about", "approximately", "substantially", and "in the order of" signify plus or minus 10%, preferably plus or minus 5% or, when an angular value is concerned, plus or minus 10°, preferably 5°.

Figure 1:
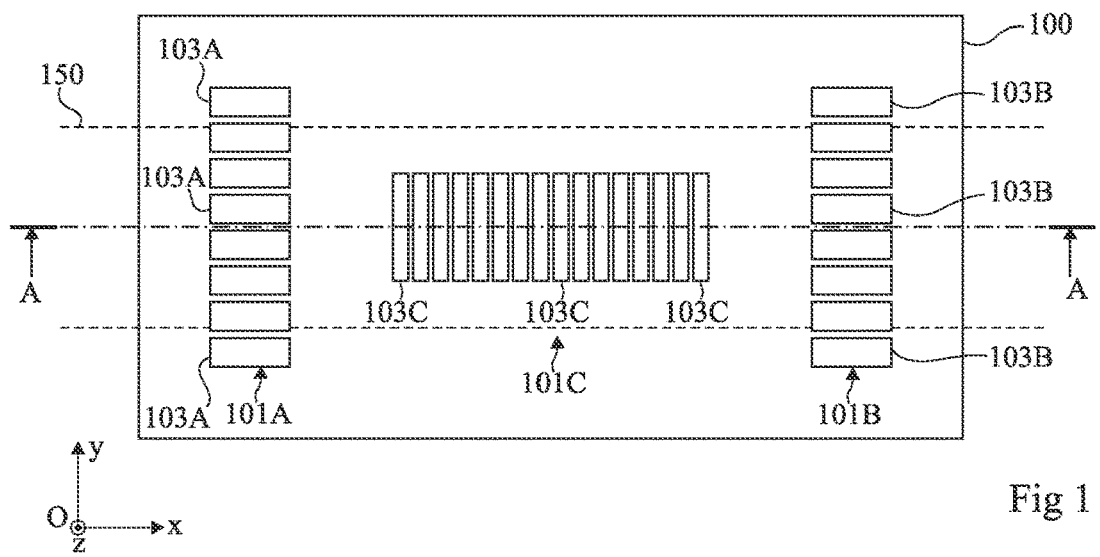
FIG. 1 is a top view schematically and partially illustrating an example of a portable electronic device of cardiovascular activity assessment according to an embodiment.

FIG. 1 is a top view schematically and partially illustrating an example of a portable electronic device 100 for assessing the cardiovascular activity by means of ultrasounds according to an embodiment.

In the shown example, device 100 comprises first, second, and third probes 101A, 101B, 101C, each comprising an array of ultrasound transducers 103A, respectively 103B, respectively 103C. In the shown example, the arrays of transducers 103A, 103B, and 103C are substantially linear. As a variant, each array of transducers 103A, 103B, and 103C may have a non-rectilinear shape, for example, curved. Further, there has been illustrated in FIG. 1 an example where the transducers 103A, 103B, 103C of a same array have substantially identical outer dimensions, to within manufacturing dispersions, and are regularly spaced apart. However, as a variant, the transducers 103A, 103B, 103C of a same array may have dimensions different from one another and a variable spacing.

The first and second ultrasound probes 101A, 101B are located on either side of the third ultrasound probe 101C and are substantially parallel to each other. The third ultrasound probe 101C is substantially perpendicular to the first and second probes 101A, 101B. In this example, the first, second, and third probes 101A, 101B, 101C have, in top view, a general H shape, the first and second probes 101A, 101B respectively forming the two vertical bars of the H and the third probe 101C forming the horizontal bar of the H.

In the example illustrated in FIG. 1, probes 101A, 101B each comprise eight ultrasound transducers 103A, 103B, and probe 101C comprises sixteen ultrasound transducers 103C. However, probes 101A, 101B, 101C may comprise numbers of ultrasound transducers 103A, 103B, 103C different from those shown. As an example, the number of ultrasound transducers 103A, 103B, 103C of each array corresponds to a power of two and the number of ultrasound transducers 103C of central probe 101C is twice greater than the number of ultrasound transducers 103A, 103B of each of the two lateral probes 101A, 101B. Ultrasound transducers 103A, 103B, 103C for example each have a substantially rectangular shape. Further, transducers 103C may be narrower than transducers 103A, 103B so that probe 101C has a higher lateral resolution than probes 101A, 101B, for example in a case where probe 101C is used in B-mode, or to perform an electronically-steered Doppler shot, and probes 101A, 101B are used in A-mode as will be discussed in further detail hereafter.

In the shown example, portable electronic device 100 is arranged above a blood vessel 150, for example, an artery, having a wall symbolized, in FIG. 1, by two dotted lines. For simplification, the thickness of blood vessel 150 is neglected, and the two dotted lines of FIG. 1 can thus indifferently symbolize the inner or outer walls of blood vessel 150. In this example, the arrays of ultrasound transducers 103A, 103B of the first and second probes 101A, 101B are oriented transversely with respect to blood vessel 150, and the array of ultrasound transducers 103C of third probe 101C is oriented longitudinally with respect to blood vessel 150. More precisely, in this illustrated example, the array of ultrasound transducers 103C is substantially parallel to an axis Ox, along which blood vessel 150 laterally extends, while the arrays of ultrasound transducers 103A, 103B are substantially parallel to an axis Oy, perpendicular to axis Ox. As an example, in a case where device 100 is worn on a user's arm or wrist, blood vessel 150 is the ulnar artery.

For simplification, these has been shown in FIG. 1 an example where blood vessel 150 is substantially rectilinear and has a cross-section having for example a circular shape and substantially constant dimensions along its entire length. However, in practice, blood vessel 150 may have any shape, for example, a curved shape, and a cross-section having a shape and dimensions which are variable along all or part of its length. Further, there has been shown in FIG. 1 an example where the arrays of ultrasound transducers 103A, 103B, 103C are substantially centered with respect to blood vessel 150. This example is however not limiting, and the arrays of ultrasound transducers 103A, 103, 103C may be off-centered, for example, shifted along axis Oy, with respect to blood vessel 150.

For the readability of the drawing, there has been illustrated in FIG. 1 an example where blood vessel 150 has a diameter greater than the length (dimension taken along axis Oy) of transducers 103C. Blood vessel 150 may however have different proportions than transducers 103C, for example a diameter substantially equal to the length of transducers 103C, or a diameter smaller than the length of transducers 103C.

Figure 2:
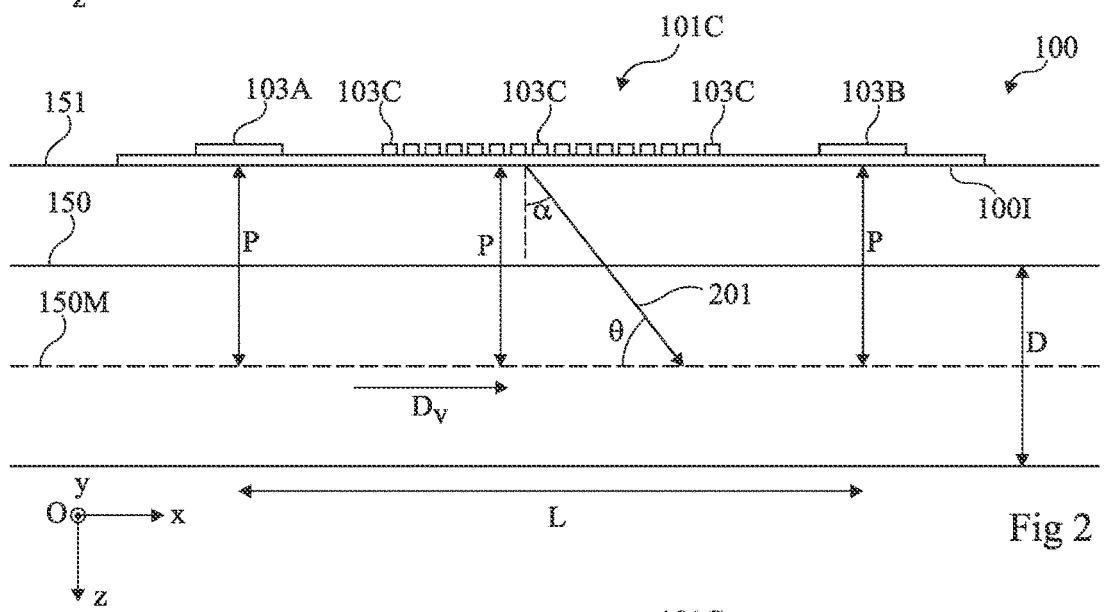
FIG. 2 is a cross-section view, along plane AA of FIG. 1, of the device of FIG. 1 in a first configuration of use.

FIG. 2 is a cross-section view, along plane AA of FIG. 1, of the portable electronic device 100 of human cardiovascular activity assessment in a first configuration of use.

In this configuration of use, blood vessel 150 is substantially parallel to a substantially planar lower surface 1001 of device 100. More precisely, blood vessel 150 has a median axis 150M parallel to axis Ox, the lower surface 1001 of device 100 being parallel to plane Oxy. In the shown example, ultrasound transducers 103A, 103B, 103C are substantially equidistant from the median axis 150M of blood vessel 150. In other words, in this example, blood vessel 150 extends laterally under ultrasound transducers 103A, 103B, 103C at a substantially constant depth P. In the orientation of FIG. 2, depth P corresponds to a distance measured along vertical axis Oz, between the lower surface 1001 of device 100 and the median axis 150M of blood vessel 150. As an example, the lower surface 1001 of device 100 is placed on top of and in contact with the skin of a user's arm 151.

The ultrasound transducers 103A, 103B of the probes 101A, 101B of device 100 for example enable to estimate a volume flow rate $D_v$ of blood flowing within the portion of blood vessel 150 located under device 100, for example by a pulse wave velocity (PWV) method. The pulse wave velocity, noted VOP, is for example calculated based on a measurement of the pulse transit time (PTT) generated at each heartbeat, between ultrasound transducers 103A and 103B.

For this purpose, device 100 records for example time variations DA(t), DB(t) of a diameter D of the assessed blood vessel at two distinct locations separated by a distance L, for example vertically in line with probes 101A and 101B. A measurement of phase shift Δt between the time variations DA(t), DB(t) of diameter D, respectively recorded due to probes 101A and 101B after a same heartbeat, enables to estimate the propagation time of the pulse wave between these probes. Knowing the distance L separating probes 101A and 101B, the propagation velocity of pulse wave VOP within blood vessel 150 can then be obtained (VOP=L/Δt).

As an example, the time variations DA(t), DB(t) of the diameter D of blood vessel 150 are estimated in A-mode. In this mode, an amplitude of a returned echo signal is measured according to depth. As a variant, the time variations DA(t), DB(t) of the diameter D of blood vessel 150 may be assessed from images obtained in B-mode. In this mode, two-dimensional ultrasound scan images formed of bright spots representing ultrasound echoes are formed, the luminosity of each spot being determined by the amplitude of the returned echo signal.

Further, the ultrasound transducers 103C of third probe 101C may enable to estimate the volume flow rate $D_v$ of the blood flowing within the portion of blood vessel 150 located under device 100. The estimation of flow rate $D_v$ by probe 101C is for example performed by Doppler effect.

In this case, ultrasound transducers 103C are for example controlled to emit an incident ultrasound beam 201 towards blood vessel 150, and to receive an ultrasound beam reflected by the blood flowing within blood vessel 150. The incident ultrasound beam 201 for example corresponds to a pulse signal of frequency $f_i$ and the reflected ultrasound beam for example corresponds to a pulse signal of frequency $f_r$. By measuring a frequency shift between the incident and reflected signals, that is, by measuring a difference between frequencies $f_r$ and $f_i$, the velocity v of displacement of blood within blood vessel 150 is obtained. Further, the measurements of diameter D enable to estimate a cross-section area S of blood vessel 150 under device 100. Cross-section S for example corresponds to a surface area of a transverse cross-section of blood vessel 150. By multiplying the cross-section area S of blood vessel 150 by the blood flow velocity v through this cross-section area, the volume flow rate $D_v$ of blood within blood vessel 150 ($D_v=S*v$) can then be obtained.

As an example, the diameter D of blood vessel 150 is estimated, in mode A or in mode B, by the ultrasound transducers 103C of probe 101C. As a variant, the diameter D of the blood vessel may be estimated, in mode A or in mode B, by the ultrasound transducers 103A of probe 101A and/or by the ultrasound transducers 103B of probe 101B as previously discussed.

During the estimation of blood flow rate $D_v$ by Doppler effect, the incident ultrasound beam 201 emitted by the array of ultrasound transducers 103C has an emission direction for example forming an angle, called steering angle α, with respect to a normal to the lower surface 1001 of device 100.

To obtain an optimal accuracy of measurement of velocity v, angle α is for example adjusted so that ultrasound beam 201 reaches blood vessel 150 under a low angle of incidence θ, called Doppler angle. As an example, angle θ is in the range from 30° and 60°.

Further, incident ultrasound beam 201 is for example focused on the level of the median axis 150M of blood vessel 150, that is, on depth P under device 100, in this example. This for example enables to measure the velocity v at the center of the flow and not close to the walls of blood vessel 150. This results in a better measurement accuracy.

As a variant, probe 101C may be used to perform B-mode ultrasound scan imaging, more precisely plane wave imaging (PWI) at high acquisition frequency. Based on the images thus obtained, the diameter D of blood vessel 150 and the blood flow velocity v may for example be estimated by a technique called vector flow imaging (VFI).

Figure 3:
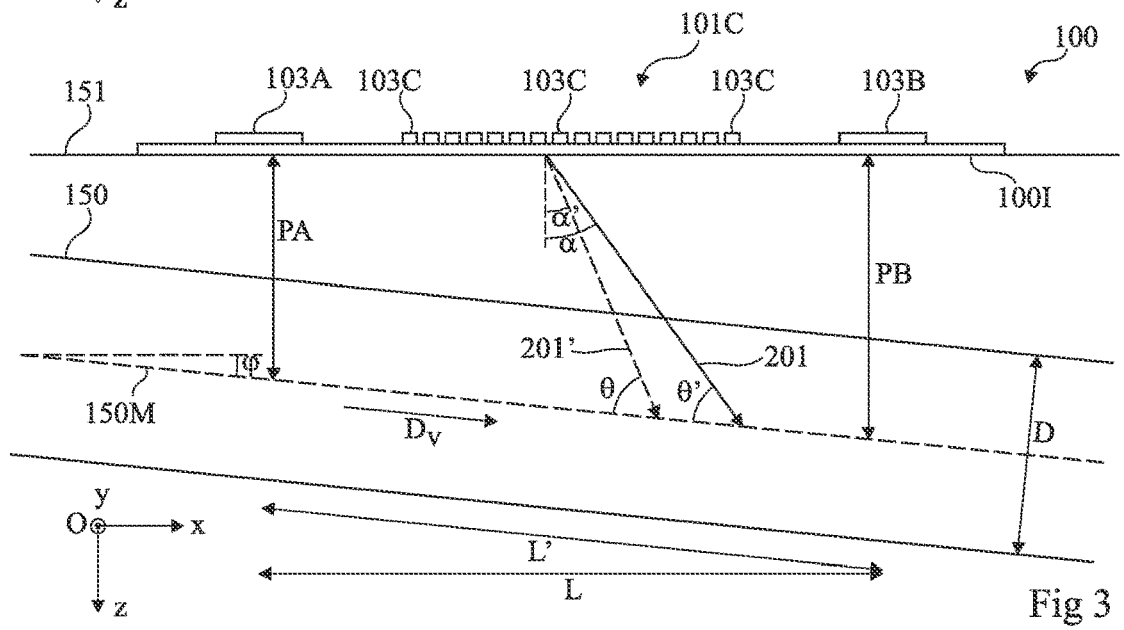
FIG. 3 is a cross-section view, along plane AA of FIG. 1, of the device of FIG. 1 in a second configuration of use.

FIG. 3 is a cross-section view, along plane AA of FIG. 1, of the portable electronic device 100 of human cardiovascular activity assessment in a second configuration of use.

In this configuration of use, blood vessel 150 is inclined with respect to device 100. More precisely, blood vessel 150 is, in this example, parallel to plane Oxz and inclined by an angle φ relative to horizontal axis Ox, the lower surface 1001 of device 100 being parallel to plane Oxy. In this example, the ultrasound transducers 103B of second probe 101B are more distant from the median axis 150M of blood vessel 150 than the ultrasound transducers 103A of first probe 101A. More precisely, in the example illustrated in FIG. 3, the median axis 150M of blood vessel 150 is located at a depth PA under ultrasound transducers 103A and at another depth PB, greater than depth PA, under ultrasound transducers 103B. In the orientation of FIG. 3, depths PA, PB correspond to distance measurements along vertical axis Oz.

In the example illustrated in FIG. 3, the inclination of blood vessel 150 modifies the angle of incidence of the incident ultrasound beam 201 emitted by probe 101C towards blood vessel 150. More precisely, in this example, beam 201 reaches blood vessel 150 under an angle of incidence θ' smaller than angle θ (θ'=θ+φ). This tends to degrade the accuracy of the measurement of velocity v, and thus the estimation of the volume flow rate $D_v$ of blood within blood vessel 150.

Further, in the example illustrated in FIG. 3, the angle of inclination of blood vessel 150 tends to cause a focusing of the incident ultrasound beam 201 emitted by probe 101C on an area distant from median axis 150M, that is, closer to the walls of blood vessel 150M than in the example illustrated in FIG. 2. This also tends to degrade the accuracy of the measurement of velocity v, and thus of flow rate $D_v$.

According to an embodiment, advantage is taken of the lateral arrays of ultrasound transducers 103A, 103B located on either side of the central array of ultrasound transducers 103C to emit ultrasound beams enabling to estimate the position of blood vessel 150 with respect to device 100. According to the estimated position of blood vessel 150, the ultrasound beam 201 emitted by third probe 101C is then adjusted.

More precisely, ultrasound transducers 103An emit for example a first ultrasound beam enabling to estimate the position, for example, the depth PA along axis Oz, at which blood vessel 150 is located vertically in line with probe 101A. Similarly, ultrasound transducers 103B emit for example a second ultrasound beam enabling to determine the position, for example, the depth DB along axis Oz, at which blood vessel 150 is located vertically in line with probe 101B. Based on depths PA and PB, and knowing the distance L separating probes 101A and 101B, the angle φ of inclination of blood vessel 150 with respect to axis Ox can be obtained, for example by considering that the portion of blood vessel 150 located under device 100 is substantially rectilinear. The estimation of the angle φ thus obtained for example enables to advantageously compensate for the inclination of blood vessel 150 during the measurement of velocity v by Doppler effect, for example by emitting with central probe 101C an incident ultrasound beam 201' forming an angle α' with the normal to the lower surface 1001 of device 100. Angle α' is for example adjusted so that ultrasound beam 201' reaches blood vessel 150 under an angle of incidence as close as possible to angle θ (equal to angle θ, in the example illustrated in FIG. 3).

The estimation of angle φ, due to the lateral probes 101A, 101B of device 100, further enables to modify a focal distance of the incident ultrasound beam emitted by central probe 101C. In the shown example, incident ultrasound beam 201' is focused in the vicinity of the median axis 150M of blood vessel 150, which here again enables to compensate for the inclination of blood vessel 150 with respect to device 100 and to advantageously obtain more accurate measurements than if probe 101C emitted ultrasound beam 201.

Further, the ultrasound beams emitted by lateral probes 101A, 101B may be adjusted according to the estimated position of blood vessel 150. More precisely, an emission direction and a focal distance of the ultrasound beams respectively emitted by the arrays of ultrasound transducers 103A, 103B can be adjusted according to the estimated position of blood vessel 150. As a variant, once the position of blood vessel 150 has been detected by probes 101A, 101B, a portion only of ultrasound transducers 103A, 103B, for example the ultrasound transducer 103A, 103B of each array closest to median axis 150M, may be used to follow the time variation of diameter D.

In the case where probes 101A, 101B implement the method of pulse wave velocity determination by measurement of the pulse transit time previously described in relation with FIG. 2, the estimation of the position of blood vessel 150 with respect to device 100 may further be advantageously used to compensate for a distance error between the areas of measurement of diameter D vertically in line with ultrasound transducers 103A, 103B. In the example of FIG. 3, these areas are indeed separated by a distance L' which is not equal to distance L between probes 101A and 101B, as in the example illustrated in FIG. 2, but equal to $L*\cos(\varphi)$.

There has been illustrated in FIG. 3 an example where the median axis 150M of blood vessel 150 is inclined by a negative angle φ relative to axis Ox and where ultrasound beam 201' is directed downstream of blood vessel 150 (rightwards, in the orientation of FIG. 3). As a variant, blood vessel 150 may be inclined by a positive angle φ relative to axis Ox, depth PA being in this case greater than depth PB. The compensation of the inclination of blood vessel 150 would then be performed, for example, by adjusting angle α' so that ultrasound beam 201' reaches blood vessel 150 under an angle of incidence between 120 and 150°. In this case, ultrasound beam 201' would be directed upstream of blood vessel 150 (leftwards, in the orientation of FIG. 3).

Although an example where blood vessel 150 is parallel to plane Oxz and inclined with respect to angle Ox has been described hereabove, the described embodiments also apply to cases where blood vessel 150 has any orientation in space. As an example, the described embodiments may be transposed by those skilled in the art to cases where blood vessel 150 is parallel to plane Oxy and inclined with respect to axis Ox and to cases where blood vessel 150 is parallel neither to plane Oxz, nor to plane Oxy.

Further, there have been described hereabove embodiments where the direction and/or the focal distance of the ultrasound beams emitted by the arrays of ultrasound transducers 103A, 103B, 103C may be adjusted according to the estimated position of blood vessel 150. However, it would also be possible to take advantage of the estimation of the position of blood vessel 150 with respect to device 100 to compensate for measurements performed by probes 101A, 101B, 101C without modifying the direction and/or the focal distance of the ultrasound beams that they emit, or as a complement to such modifications.

Further, although an example where the two lateral arrays of transducers 103A and 103B are used to estimate the position of blood vessel 150 has been described, one may, as a variant, provide using a single lateral array of transducers, for example the transducers 103A of probe 101A or the transducers 103B of probe 101B, to estimate the position of blood vessel 150. This variant is within the abilities of those skilled in the art based on the indications of the present disclosure.

Figure 4:
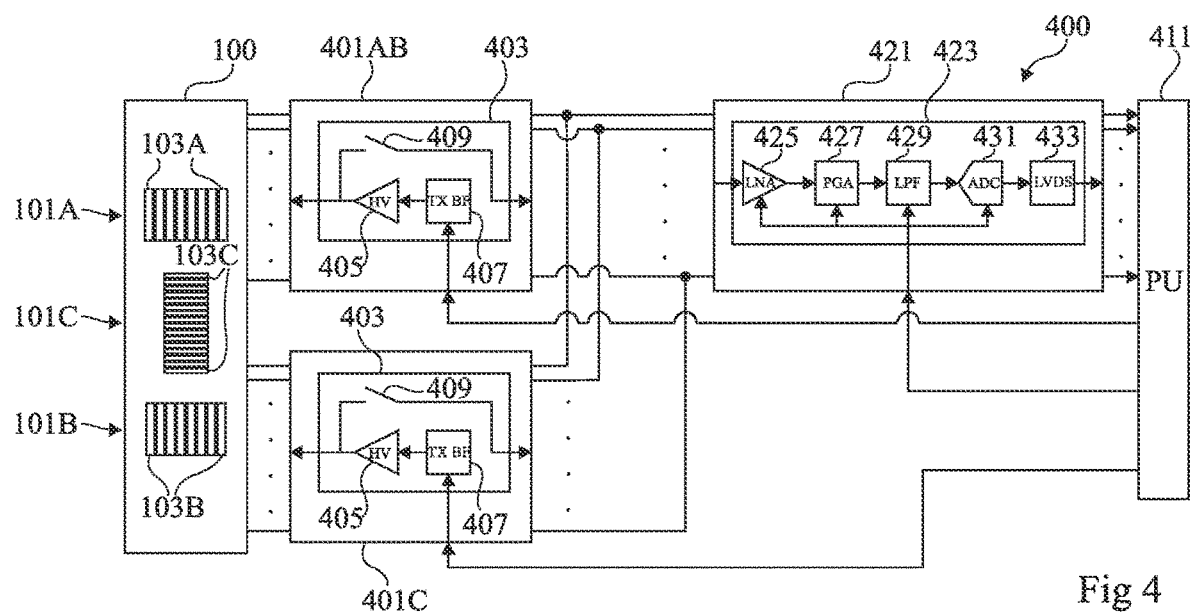
FIG. 4 schematically and partially shows an example of embodiment of a circuit for controlling the device of FIG. 1.

FIG. 4 schematically and partially shows an example of embodiment of a control circuit 400 of the device 100 of FIG. 1.

In the shown example, circuit 400 comprises two pulsers 401AB, 401C, also called transmit circuits. Pulser 401AB is for example connected to the ultrasound transducers 103A, 103B of lateral probes 101A, 101B and pulser 401C is for example connected to the ultrasound transducers 103C of central probe 101C. In this example, each pulser 401AB, 401C comprises, for each ultrasound transducer 103A, 103B, 103C to which it is connected, a path 403. As an example, in the case where the arrays of lateral probes 101A, 101B each comprise eight ultrasound transducers 103A, 103B and where the array of central probe 101C comprises sixteen ultrasound transducers 103C, each pulser 401AB, 401C comprises sixteen identical paths 403, to within manufacturing dispersions. As an example, pulsers 401AB and 401C are identical, to within manufacturing dispersions.

In the shown example, each path 403 more precisely comprises an amplifier 405 (HV), for example a high-voltage amplifier, a transmit beamformer 407 (TX BF) and a transceiver switch 409. In the example illustrated in FIG. 4, transmit beamformer 407 comprises an input connected to an output of a processing unit 411 (PU), for example, a field-programmable gate array (FPGA), and an output connected to an input of high-voltage amplifier 405. Amplifier 405 comprises an output connected to one of the terminals of switch 409 and to one of ultrasound transducers 103A, 103B, 103C. In this example, the other terminal of each switch 409 is connected to an analog front-end circuit 421, also called receive circuit.

Receive circuit 421 comprises a plurality of receive paths 423. In this example, circuit 421 comprises a number of receive paths 423 equal to half the number of ultrasound transducers 103A, 103B, 103C of device 100. As an example, in the case where the arrays of lateral probes 101A, 101B each comprise eight ultrasound transducers 103A, 103B and where the array of central probe 101C comprises sixteen ultrasound transducers 103C, circuit 421 comprises sixteen identical paths 423, to within manufacturing dispersions.

In the shown example, each path 423 more precisely comprises an amplifier 425 (LNA), for example, a low-noise amplifier, an amplifier 427 (PGA), for example, a programmable gain amplifier, a low-pass filter 429 (LPF), an analogto-digital converter 431 (ADC), and a series converter 433 (LVDS), for example, a converter capable of operating in low-voltage differential signalling. In this example, the amplifier 425 of each path 423 comprises an input connected to one of the paths 403 of pulser 401AB and to one of the paths 403 of pulser 401C, and an output connected to an input of amplifier 427. Amplifier 427 comprises an output connected to an input of filter 429. Converter 431 comprises an input connected to filter 429 and an output connected to an input of series converter 433. In the shown example, amplifiers 425 and 427, filter 429 and converter 431 each comprise a control input connected to an output of processing unit 411. Further, each path 423 of circuit 421 comprises an output, corresponding to an output of series converter 433, connected to processing unit 411.

An example of operation of the device 100 associated with circuit 400 will now be described in relation with FIG. 4.

During a first emission step, the switches 409 of pulser 401AB are for example all in the off state and ultrasound beams are emitted by lateral probes 101A and 101B. During the first emission step, processing unit 411 is for example configured to transmit no signal to the transmit beamformers 407 of pulser 401C, probe 101C then emitting no ultrasound beam. Then, during a first reception step subsequent to the first emission step, all the switches 409 of pulser 401AB are for example turned off to enable lateral probes 101A, 101B to capture ultrasound echoes. In this example, the position of blood vessel 150 with respect to device 100 is for example estimated at the end of the first reception step.

Then, during a second emission step subsequent to the first reception step, all the switches 409 of pulser 401C are in the off state and ultrasound beams are emitted by central probe 101C. During the second emission step, processing unit 411 is for example configured to transmit no signal to the formers of the emission beams 407 of pulser 401AB, probes 101A and 101B then for example emitting no ultrasound beam. Finally, during a second reception step subsequent to the second emission step, all the switches 409 of pulser 401C are for example turned on to enable central probe 101C to capture ultrasound echoes. The measurement of flow rate $D_v$ is for example performed at the end of the second reception step.

Once the second reception step has ended, it is for example proceeded to the adjustment of emission parameters of the beam emitted by central probe 101C and/or of the beams emitted by probes 101A, 101B according to the position of blood vessel 150 with respect to device 100 such as estimated during the first reception step. The previously-described transmission and reception steps may for example be repeated by using the modified emission parameters.

As an example, the position of blood vessel 150 is estimated and the emission parameters of probe 101C and/or of probes 101A, 101B are modified at the beginning of a phase of assessment of a patient's cardiovascular activity, the emission parameters of probe 101C and/or of probes 101A, 101B remaining unchanged afterwards until the next assessment phase, for example carried out on another patient. As a variant, it may be provided for the operations of estimation of the position of blood vessel 150 and of adjustment of the emission parameters of probe 101C and/or of probes 101A, 101B to be repeated during a same phase of assessment of the patient's cardiovascular activity.

Figure 5:
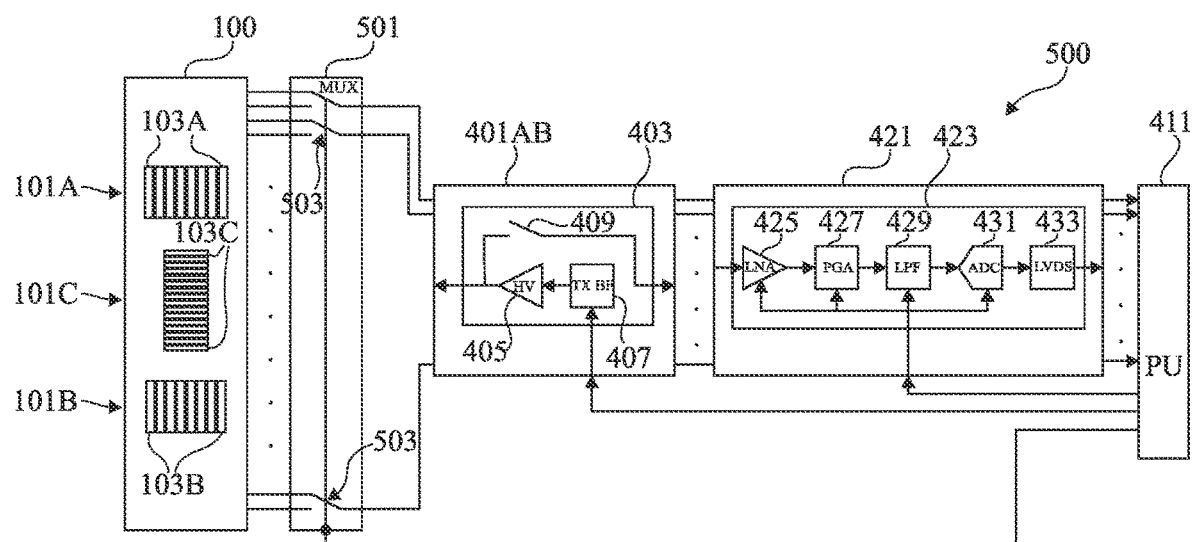
FIG. 5 schematically and partially shows another example of embodiment of the control circuit of the device of FIG. 1.

FIG. 5 schematically and partially shows an example of embodiment of a control circuit 500 of the device 100 of FIG. 1. The circuit 500 of FIG. 5 comprises elements common with the circuit 400 of FIG. 4.

The circuit 500 of FIG. 5 differs from the circuit 400 of FIG. 4 mainly in that, in the shown example, circuit 500 comprises a single pulser, for example, the pulser 401AB previously described in relation with FIG. 4. Further, circuit 500 differs from circuit 400 in that it comprises a multiplexer 501 (MUX) coupling the arrays of ultrasound transducers 103A, 103B, 103C of the probes 101A, 101B, 101C of device 100 to pulser 401AB. In the shown example where the device comprises thirty-two ultrasound transducers 10A, 103B, 103C, multiplexer 501 more precisely comprises sixteen paths and is of 1-to-2 type.

As an example, each path of multiplexer 501 comprises, as in the example illustrated in FIG. 5, a switch 503 of single-pole double-throw (SPDT) type having an input terminal connected to one of the paths 403 of pulser 401AB, having a first output terminal for example connected to one of the ultrasound transducers 103A, 103B of lateral probes 101A, 101B, and having a second output terminal for example connected to one of the ultrasound transducers 103C of central probe 101C. Multiplexer 501 further comprises a control input connected to processing unit 411 and for example enabling to having all the switches 503 switch between their first and second output terminals, for example, substantially simultaneously. As an example, the control input receives from processing unit 411 a control signal having a first level placing all the switches 503 in a state where their input terminal is connected to their first output terminal and having a second level placing all the switches 503 in another state where their input terminal is connected to their second output terminal.

An example of operation of the device 100 associated with circuit 500 will now be described in relation with FIG. 5.

During a first emission step, the switches 409 of pulser 401AB are for example all in the off state, the switches 503 of multiplexer 501 are for example placed in the state where their input terminal is connected to their first output terminal, connected to ultrasound transducers 103A, 103B in this example, and ultrasound beams are emitted by lateral probes 101A and 101B. Then, during a first reception step subsequent to the first emission step, all the switches 409 of pulse generator 401AB are for example turned on to enable lateral probes 101A, 101B to capture ultrasound echoes, the switches 503 of multiplexer 501 remaining in the state where there input terminal is connected to their first output terminal. In this example, the position of blood vessel 150 with respect to device 100 is for example estimated at the end of the first reception step.

Then, during a second emission step subsequent to the first reception step, all the switches 409 of pulser 401AB are for example off, the switches 503 of multiplexer 501 are for example switched to the state where their input terminal is connected to their second output terminal, connected to ultrasound transducers 103C in this example, and ultrasound beams are emitted by central probe 101C. Then, during a second reception step subsequent to the second emission step, all the switches 409 of pulse generator 401AB are for example turned on to enable central probe 101C to capture ultrasound echoes, the switches 503 of multiplexer 501 remaining in the state where their input terminal is connected to their second output terminal, to enable central probe 101C to capture ultrasound echoes. The measurement of flow rate $D_v$ is for example performed at the end of the second reception step.

Once the second reception step has ended, it is for example proceeded to the adjustment of emission parameters of the beam emitted by central probe 101C and/or of the beams emitted by probes 101A, 101B according to the estimated position of blood vessel 150 with respect to device 100. The previously-described emission and reception steps may then for example be repeated by using the modified emission parameters.

An advantage of the previously-described circuits 400, 500 lies in the fact that they have a small number of electronic components and of paths, which makes circuits 400, 500 and device 100 compatible with an integration in a portable device and having a low acquisition cost.

Figure 6:
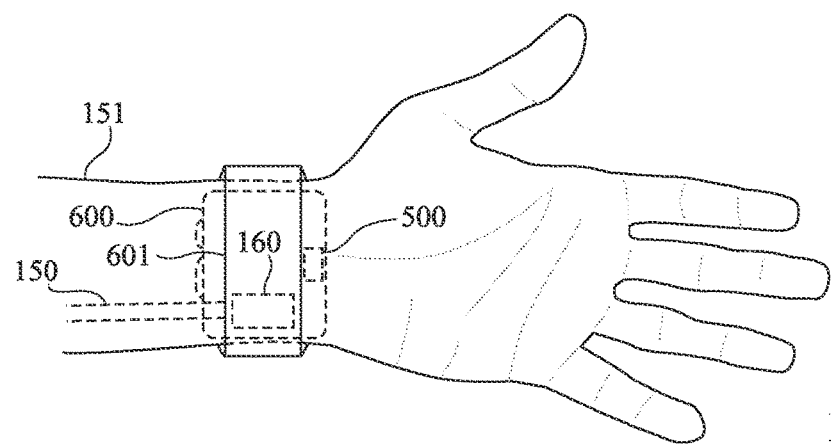
FIG. 6 illustrates an example of integration of the device of FIG. 1 in a smart watch worn on a user's wrist.

FIG. 6 illustrates an example of integration of the device 100 of FIG. 1 in a device 600 of the type of a bracelet worn on a user's arm 151, for example, a smart watch. In the shown example, device 600 further integrates the control circuit 500 of FIG. 100. Device 100 is for example located in an area of device 600 intended to be placed substantially in front of the ulnar artery 150 of the user's arm 151. As an example, device 100 is integrated in a bracelet 601 of device 600.

Various embodiments and variants have been described. Those skilled in the art will understand that certain features of these various embodiments and variants may be combined, and other variants will occur to those skilled in the art. In particular, those skilled in the art are capable of replacing the control circuit 500 of the device 600 of FIG. 6 with the control circuit 400 previously described in relation with FIG. 4.

Finally, the practical implementation of the described embodiments and variants is within the abilities of those skilled in the art based on the functional indications given hereabove. In particular, the practical forming of device 100, for example, the geometry, the positioning, and the control of the ultrasound transducers 103A, 103B, 103C of the probes 101A, 101B, 101C of device 100, and the driving of the elements of circuits 400, 500 by processing unit 411 are within the abilities of those skilled in the art based on the indications of the present disclosure.

What is claimed is:

1. A portable electronic device for assessing a human cardiovascular activity, comprising first and second probes substantially parallel to each other and located on either side of a third probe, substantially perpendicular to the first and second probes, each probe comprising an array of ultrasound transducers, and a control circuit configured to:
   a) estimate, by means of a first ultrasound beam emitted by the first probe, a position of a blood vessel with respect to the device; and
   b) adjust a second ultrasound beam, emitted by the third probe, according to the estimated position of the blood vessel.

2. The portable electronic device according to claim 1, wherein the control circuit is configured to, at step b), adjust a direction of emission of the second ultrasound beam according to the estimated position of the blood vessel.

3. The portable electronic device according to claim 1, wherein the control circuit is further configured to, at step b), adjust focal distance of the second ultrasound beam according to the estimated position of the blood vessel.

4. The portable electronic device according to claim 1, wherein the control circuit is configured to adjust the first ultrasound beam emitted by the first probe according to the estimated position of the blood vessel.

5. The portable electronic device according to claim 1, wherein the second probe is configured to emit a third ultrasound beam.

6. The portable electronic device according to claim 5, wherein the control circuit is further configured to, during step a), estimate the position of the blood vessel with respect to the device by means of the third ultrasound beam emitted by the second probe.

7. The portable electronic device according to claim 5, wherein the control circuit is configured to estimate a pulse wave velocity inside of the blood vessel based on the first and third ultrasound beams respectively emitted by the first and second probes.

8. The portable electronic device according to claim 1, wherein the control circuit is further configured to estimate the blood flow rate inside of the blood vessel, based on the second ultrasound beam, by Doppler effect.

9. The portable electronic device according to claim 1, wherein the blood vessel is the ulnar artery.

10. The portable electronic device according to claim 1, wherein the control circuit comprises a first pulser connected to the ultrasound transducers of the arrays of the first and second probes and a second pulser connected to the ultrasound transducers of the array of the third probe.

11. The portable electronic device according to claim 1, wherein the control circuit comprises a single pulser coupled, via a multiplexer, to the ultrasound transducers of the arrays of the first, second, and third probes.

12. The portable electronic device according to claim 11, wherein the array of ultrasound transducers of the third probe comprises twice more ultrasound transducers than each of the arrays of ultrasound transducers of the first and second probes, the multiplexer being a 1-to-2 multiplexer.

13. A connected watch or bracelet comprising the portable electronic device according to claim 1.

14. A method of assessment of a human cardiovascular activity, by a portable electronic device comprising first and second probes substantially parallel to each other and located on either side of a third probe, substantially perpendicular to the first and second probes, each probe comprising an array of ultrasound transducers, and a control circuit configured to:
   a) estimate, by means of a first ultrasound beam emitted by the first probe, a position of a blood vessel with respect to the device; and
   b) adjust a second ultrasound beam, emitted by the third probe, according to the estimated position of the blood vessel.

15. The method according to claim 14, wherein, at step a), the position of the blood vessel with respect to the device is further estimated by a third ultrasound beam emitted by the second probe.

* * * * *